United States Patent
Schraga

[11] Patent Number: 5,908,434
[45] Date of Patent: Jun. 1, 1999

[54] LANCET DEVICE

[76] Inventor: Steven Schraga, 9433 Byron Ave., Surfside, Fla. 33154

[21] Appl. No.: 09/025,292

[22] Filed: Feb. 13, 1998

[51] Int. Cl.[6] .................................................. A61B 17/14
[52] U.S. Cl. .......................................... 606/181; 606/182
[58] Field of Search .................................... 606/181, 182, 606/183, 184, 185, 186; 604/136

[56] References Cited

U.S. PATENT DOCUMENTS

| | | | |
|---|---|---|---|
| 2,711,738 | 6/1955 | Kelly et al. ............................... | 606/181 |
| 5,147,375 | 9/1992 | Sullivan et al. .......................... | 606/182 |
| 5,439,473 | 8/1995 | Jorgensen ................................. | 606/182 |

*Primary Examiner*—Michael Buiz
*Assistant Examiner*—Vy Quang Bui
*Attorney, Agent, or Firm*—Malloy & Malloy, P.A.

[57] ABSTRACT

A lancet device used to pierce a user's skin and including a lancet with a body portion and a piercing tip, a primary housing, a cover assembly with a piercing opening and structured to be matingly coupled with the primary housing to define an interior chamber, and a lancet receiving assembly movably disposed within the interior chamber and structured and disposed to hold the lancet during its driven movement between a cocked orientation, a piercing orientation and a fired orientation. The lancet device further includes a retention member including a pair of elongate fingers, and an engagement hub disposed in the interior chamber and structured to be cooperatively engaged by inwardly depending protrusions on the elongate fingers when the lancet receiving assembly is in the cocked orientation so as to maintain the lancet receiving assembly in the cocked orientation until the retention member is affirmatively released from its cooperative engagement with the engagement hub by an exteriorly actuatable actuation assembly which urges the elongate fingers out of their engagement with cooperative structure on the engagement hub.

23 Claims, 2 Drawing Sheets

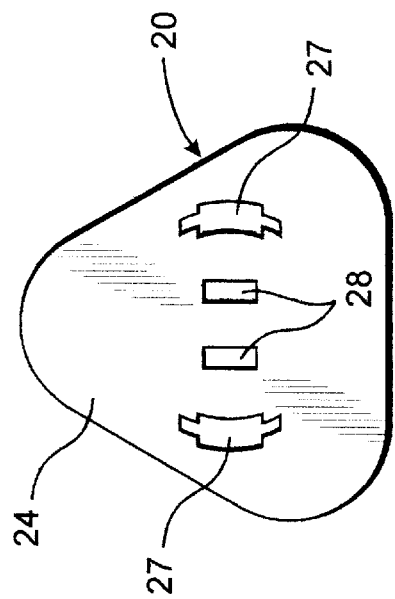
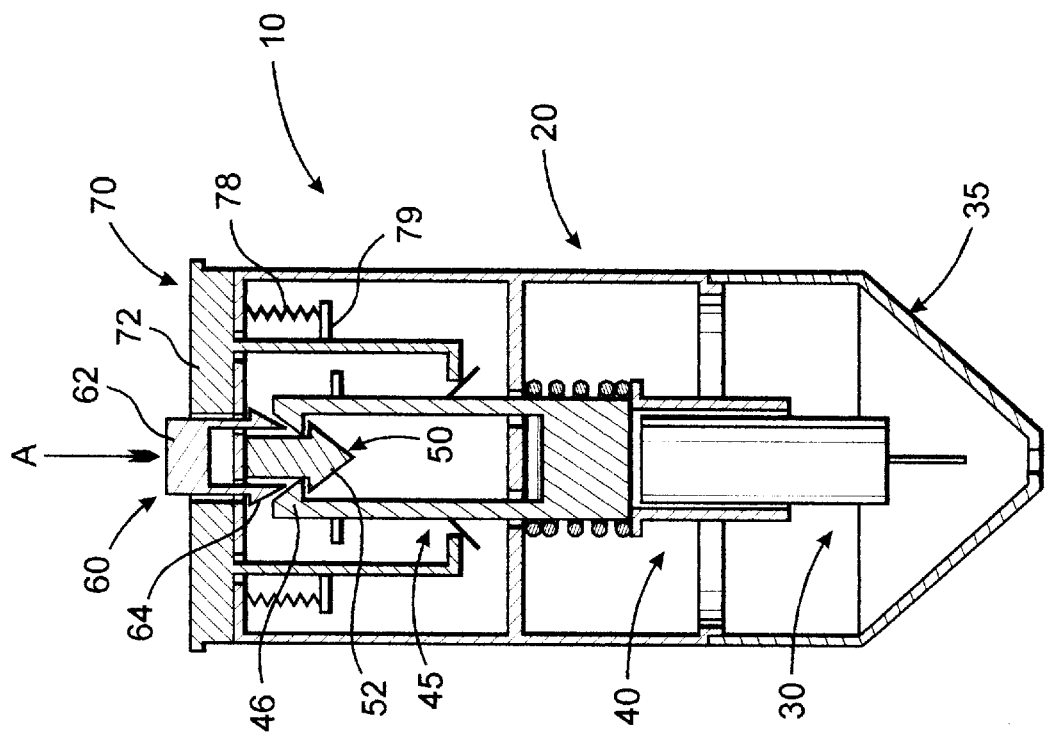

LANCET DEVICE

BACKGROUND OF THE INVENTION

1. Field of the Invention

The present invention relates to a lancet device, and in particular a mini lancet device which is structured in such a manner as to be manufacturable in a small, compact configuration, yet which is substantially easy to use and is effective to pierce a user's skin, such as at a finger for conducting a blood test. Furthermore, the lancet device is easy to manipulate and actuate, and is structured in a manner which facilitates accurate determination that the device is in a ready to use orientation.

2. Description of the Related Art

The field of art associated with lancet devices is quite crowded, with a variety of often complex and intricate structures being utilized to drive a piercing tip of a lancet into the flesh of a patent. In particular, the typical lancet device generally utilizes a disposable lancet, often of a standard dimension, contained in a housing for firing. As such, a variety of different, full size lancet devices have been provided, some providing for re-use through internal or external cocking of the firing mechanism and providing an actuation button on a side thereof for triggering of the piercing action.

In addition to the conventional, elongate, full-size lancet devices, however, there is also the need for compact "mini" lancet devices which are substantially small and manageable, yet which are equally as effective as the larger, full size lancet devices. For example, when designing either a full-size or a mini lancet device, some primary concerns associated therewith include its economy of use and manufacture, the minimize of malfunctions or mis-fires, and various safety considerations such as those associated with inadvertent usage, incorrectly perceived malfunctions or accidental re-use of a used and possibly contaminated device. While many designs do seek to address one or more of these concerns, however, there is still a need for a device which effectively addresses all of these concerns, and which can be effectively configured in both a full size or a mini configuration.

In particular, a primary drawback associated with the mini lancet devices relates to its limited internal space, and as such, its inability to utilize various existing design features associated with the larger, full-size devices. For example, known mini device have not been able to utilize or incorporate a safe and effective structure to enable facilitated cocking or re-cocking of the lancet device. Specifically, as with the larger full-size lancet devices, it would be beneficial if a user were able to cock the assembly without having to internally actuate the mechanism in close proximity to the piercing tip of the lancet, especially in a re-cocking situation wherein removal of the lancet from the device prior to re-cocking is not practical. Moreover, existing devices, both full-size and mini have not been able to provide effective structures to clearly and effectively indicate to a user, and especially an infirmed user with some vision limitations, in a tactile and easy to identify manner,that the lancet device has been effectively cocked and is ready for use, or that it has been used such that re-cocking or removal of the lancet is necessary.

As such, despite the many features which have been incorporated into full-size devices, the generally small, compact nature of the mini lancet devices, substantially limits the ability of conventional structures, a majority of which require intricate internal designs and button actuation at a side of a housing, to be merely shrunk to define a mini device. Accordingly, there is a need for an effective lancet device which is sufficiently simple in design, yet which is highly effective for use as a mini lancet device, incorporating a variety of necessary and effective features from full size devices. Moreover, there is a need for a lancet device which is substantially easy and effective to actuate, whether in a full-size or mini form, and which enables a user to clearly and safely identify the ready status of the device in either a cocked orientation or a fired orientation. Further, such a device should be cost effective to manufacture, conveniently re-useable, easily manipulable, and minimally susceptible to accidental firing as is often the case with side actuated devices.

SUMMARY OF THE INVENTION

The present invention relates to a lancet device. In particular, the lancet device includes a lancet having a body portion and a piercing tip extending from the body portion. The lancet is preferably of a conventional configuration wherein the piercing tip is structured to be extended into piercing engagement with a user, such as at their finger, in order to penetrate the skin.

The lancet device further includes a primary housing. The primary housing includes a preferably tubular configuration and is structured to be matingly coupled with a cover assembly so as to define an interior chamber of the lancet device with the cover assembly. Further defined in the cover assembly is a piercing opening. Specifically, the piercing opening is structured to be disposed adjacent an article to be pierced, and to receive the piercing tip of the lancet therethrough upon movement of the lancet into a piercing orientation.

In particular, the lancet is driven into its piercing orientation by a lancet receiving assembly. The lancet receiving assembly is structured and disposed to at least temporarily, and preferably removably hold the lancet therein. Moreover, the lancet receiving assembly, and as such the lancet held thereby, are further structured to be movably disposed within the interior chamber of the lancet device between a cocked orientation and a fired orientation. Indeed, it is the movement of the lancet receiving assembly from the cocked orientation to the fired orientation that results in driven movement of the lancet, at least temporarily, into the piercing orientation, wherein the piercing tip of the lancet protrudes through the piercing opening of the cover assembly, prior to finally reaching the concealed and shielded fired orientation.

The lancet receiving assembly also includes a retention member. Specifically, the retention member is structured to be cooperatively engaged with an engagement hub disposed in the interior chamber. For example, at least when the lancet receiving assembly is disposed in the cocked orientation, the retention member cooperatively engages the engagement hub and thereby maintains the lancet receiving assembly in the cocked orientation until the retention member is affirmatively released from that cooperative engagement. Preferably, the retention member includes at least one generally elongate finger. Moreover, the at least one elongate finger includes an inwardly depending protrusion that is structured to engage cooperative structure on the engagement hub, when the lancet receiving assembly is disposed in the cocked orientation, until affirmatively disengaged therefrom.

The lancet device of the present invention further includes an actuation assembly. The actuation assembly is exteriorly actuatable and is structured and disposed to release the retention member from its cooperative engagement with the engagement hub. Along these lines, the actuation assembly extends at least partially into the interior chamber, when actuated, and thereby temporally urges the inwardly depending protrusion of the at least one elongate finger out of its engagement with the cooperative structure on the engagement hub. As such, the lancet receiving assembly is released from its cocked orientation by the actuation assembly, whereafter it may move at least temporarily into the piercing orientation before terminating its movement in the tip concealing, fired orientation.

It is an object of the present invention to provide a lancet device which is substantially easy and cost effective to utilize and manipulate.

A further object of the present invention is to provide a lancet device which can be configured in a mini configuration, yet which is highly effective and free from malfunction.

Yet another object of the present invention is to provide a lancet device which provides for substantially easy to recognize, tactile indication if the lancet device is in a cocked and ready to fire orientation.

Also an object of the present invention is to provide a lancet device which provides for effective re-cocking thereof in a safe and effective manner, and which provides for facilitated index finger or thumb actuation when configured in a mini form.

BRIEF DESCRIPTION OF THE DRAWINGS

For a fuller understanding of the nature of the present invention, reference should be had to the following detailed description taken in connection with the accompanying drawings in which:

FIG. 3 is a cross section view of an embodiment of the lancet device of the present invention in its cocked orientation; and FIG. 4 is a plan view of a base of the primary housing of the lancet device of the present invention.

Like reference numerals refer to like parts throughout the several views of the drawings.

DETAILED DESCRIPTION OF THE PREFERRED EMBODIMENT

Figure 2:
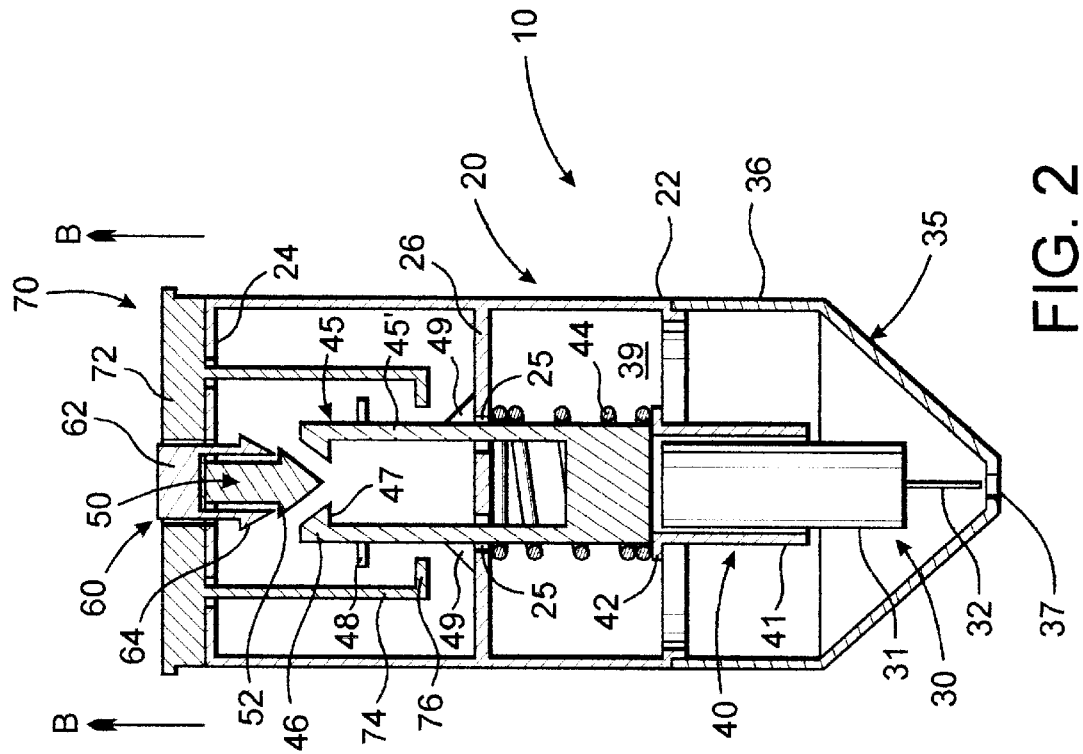
FIG. 2 is a cross section view of an embodiment of the lancet device of the present invention in its fired orientation.

Shown throughout the Figures, the present invention is directed towards a lancet device, generally indicated as 10. Specifically, the lancet device is preferably of substantially small compact configuration, thereby being generally classified as a mini lancet device, and is of the type that is utilized to prick a patient, such as on their finger, in order to do a variety of blood tests.

The lancet device 10 of the present invention includes principally a lancet 30. The lancet 30 may be of any of a number of conventional or modified configurations which are usually provided in large bulk packages in order to encourage a single use after which it may be safely discarded. In particular, the lancet 30 generally includes a body portion 31, preferably of an enlarged, tubular configuration, and a sharpened, preferably metallic piercing tip 32 extending from the body portion 31. Also, in most embodiments, the piercing tip 32 will be covered by a removable and disposable cap which is removed once the lancet 30 is presented for use in the present device.

The lancet device 10 further includes a primary housing 20. The primary housing 20 which is preferably formed of a generally rigid, tubular configuration, such as from plastic or a like material. Moreover, the primary housing 20 preferably includes a generally triangular configuration, as illustrated in the Figures, so as to facilitate grasping and manipulation thereof by a user, and so as to prevent accidental rolling thereof when the lancet device 10 is put down on a generally flat support surface.

Structured to be matingly coupled, at generally an open end 22 of the primary housing 20, is a cover assembly 35. Specifically, the cover assembly 35, which preferably includes a mating triangular configuration, is structured to be removably coupled with the primary housing 20, and terminates in a conical tip wherein a piercing opening 37 is defined. The piercing opening 37 is preferably generally centrally aligned in the cover assembly 35 and is sized so as to receive the piercing tip 32 of the lancet 30 therethrough without resistance. Moreover, the open end 36 of the cover assembly may include a flange, lip or any other conventional mating configuration to provide for effective coupled engagement with corresponding structure at the open end 22 of the primary housing 20, while also being removable if necessary for the removal and replacement of the lancet 30.

The cover assembly 35 and the primary housing 20 are further structured to define an interior chamber 39 therebetween. Furthermore, disposed within that interior chamber 39 is a lancet receiving assembly 40. Specifically, the lancet receiving assembly 40 is structured to at least temporarily hold and maintain the lancet 30 movably within the interior chamber 39. To this end, the lancet receiving assembly 40 preferably includes a holding portion 41 wherein the body portion 31 of the lancet 30 may be snugly introduced. It is understood that a variety of configurations of this holding portion 41 of the lancet receiving assembly 40 may be provided so as accommodate minor variations in the actual dimension of the body portion 31 of the lancet 30, and so as to effectively grasp the lancet 30 during utilization thereof, while also permitting safe and easy removal of the lancet 30 therefrom when use has been completed.

The lancet receiving assembly 40 is structured to be movable within the interior chamber 39 between a cocked orientation, as illustrated in FIG. 3 and a fired orientation as illustrated in FIG. 2. In particular, the cocked orientation of FIG. 3 is structured to maintain the piercing tip 32 of the lancet 30 retracted within the interior chamber 39 and in a ready to fire position. Once released from that cocked orientation, however, the lancet receiving assembly 40 is structured so as to move, at least temporarily, into a piercing orientation wherein the piercing tip 32 of the lancet 30 protrudes through the piercing opening 37 of the cover assembly 35 and into engagement with the desired surface to be pricked by the piercing tip 32. Subsequent to that temporary movement into the piercing orientation, however, the lancet receiving assembly 40 is further structured to once again generally retract into the fired orientation of FIG. 2. Accordingly, in the fired orientation, the piercing tip 32 is generally concealed within the interior chamber 39 and accidental pricking of an individual cannot occur, either as a result of a minor protrusion of the piercing tip 32 through the piercing opening 37 or of firing the lancet device 10. This retraction will be discussed in greater detail subsequently.

Looking in greater detail to the preferred structure of the lancet receiving assembly 40, it also includes a retention member 45. The retention member 45, which includes at least one, but preferably a pair of generally elongate fingers 45', is structured to be maintained within the interior chamber 39 and generally extends towards a base 24 of the primary housing 20. Moreover, each of the elongate fingers 45' of the retention member further includes an inwardly depending protrusion 47 at a tip 46 thereof. In particular, the inwardly depending protrusion 47 is structured to be cooperatively engaged with an engagement hub 50 also disposed in the interior chamber 39. Preferably, the engagement hub 50 extends into the interior chamber 39 from the base 24 of the primary housing 20. Moreover, the engagement hub 50 preferably includes a generally enlarged head 52 which defines cooperative structure that is to be cooperatively engaged by the inwardly depending protrusions 47 at the tip 46 of the elongate fingers 45' when the lancet receiving assembly 40 is disposed in its cocked orientation, as in FIG. 3. As such, the lancet receiving assembly 40 is maintained within that cocked orientation until the retention member 45, as defined by the elongate fingers 45', is affirmatively released from its cooperative engagement with the enlarged head 52 of the engagement hub 50. Moreover, since preferably two or more of the elongate fingers 45' are employed, more effective retention in the cocked orientation can be achieved, and the device is much less susceptible to accidental firing, such as if accidentally dropped and the interior components are jarred.

As illustrated in the Figures, the lancet device 10 of the present invention preferably includes a biasing element 44. The biasing element 44, which is preferably in the form of a coil spring, is structured to be disposed about the lancet receiving assembly 40. Moreover, the spring 44 is structured to be compressed within the interior chamber 39, such as between a rim 42 on the lancet receiving assembly 40 and an interior wall 26 of the primary housing 20, when the lancet receiving assembly 40 is disposed in the cocked orientation. Once the retention member 45 is released from its engagement with the engagement hub 50, however, the compressed spring 44 is free to expand and thereby fires the lancet receiving assembly 40 forward with its expansion until the piercing tip 32 of the lancet 30 protrudes through the piercing opening 37 of the cover assembly 35 to define the piercing orientation. As such, the retention member 45, as preferably defined by the elongate fingers 45', must be structured to engage the engagement hub 50 in a manner which will effectively resist the normal tendencies of the biasing element 44 to expand when the lancet receiving assembly 40 is the cocked orientation. Of course, it is clear that upon release of the retention member 45 from its cooperative engagement with the engagement hub 50, the spring 44 will expand unhindered and result in the firing of the lancet receiving assembly 40. It is noted in the Figures, that in the embodiment wherein the biasing element is compressed between the rim 42 on the lancet receiving assembly 40 and the interior wall 26 of the primary housing 20, a pair of openings 25 are preferably defined in the interior wall 26 so as to permit the free passage and slided movement of the elongate fingers 45' therethrough.

In order to release the retention member 45 from its cooperative engagement with the engagement hub 50, the lancet device 10 of the present invention further includes an actuation assembly 60. In particular, the actuation assembly 60 is exteriorly actuatable and is structured and disposed to extend at least partially into the interior chamber 39, upon actuation thereof, so as to at least temporarily urge the elongate fingers 45' out of engagement with the cooperative structure on the engagement hub 50. Specifically, the actuation assembly 60 includes an actuation head 62 which is structured to be actuated or pushed by a user, and at least one, but preferably a pair, of wedge elements 64 that extend into the interior chamber 39. The wedge elements 64 are preferably structured to generally correspond to the structure and orientation of the inwardly depending protrusion 47 on the elongate fingers 45' such that when the actuation assembly 60 is pushed down into the interior chamber 39, the wedge element 64 tends to urge the elongate fingers 45' at least temporarily into spaced apart relation from the engagement hub 50. As a result, when the wedge elements 64 outwardly urge the elongate fingers 45', the inwardly depending protrusion 47 will no longer be retained behind the enlarged head 52 of the engagement hub 50 and the lancet receiving assembly 40 is free to move into the piercing orientation and subsequently the fired orientation under the force of the biasing element 44.

Although the lancet receiving assembly 40 may normally return into the fired orientation under the natural expansion and contraction of the biasing element 44, in the preferred embodiment the lancet device 10 further includes an retraction assembly. The retraction assembly preferably includes a pair of resilient material elements 49. Moreover, these resilient material elements 49 preferably protrude from the elongate fingers 45' and are disposed so as to engage the primary housing 20, such as at the interior wall 26. Accordingly, as the lancet receiving assembly 40 is driven into its piercing orientation the driving force of the biasing element 44 is sufficient to overcome the resistance of the resilient material elements 49; however, once the piercing orientation has been reached and the biasing element 44 returns to its normal unstressed configuration, the abutted engagement of the resilient material elements 49 with the primary housing 20 results in the retraction of the lancet receiving assembly 40 into the fired orientation of FIG. 2 wherein the piercing tip 32 of the lancet 30 is substantially concealed within the cover assembly 35.

Also as illustrated in the Figures, the lancet device 10 of the present invention further includes a cocking assembly, generally indicated as 70. The cocking assembly 70 is structured to extend at least partially into the interior of the primary housing 20 so as to move the lancet receiving assembly 40 into its cocked orientation from the fired orientation. As such, the cocking assembly 70 permits exterior cocking of the lancet device 10 in order to provide for use or re-use of the lancet device 10 without having to remove the cover assembly 35 or manipulate the lancet receiving assembly 40 directly from a vicinity of the lancet 30 and the exposed piercing tip 32. In the preferred embodiment, the cocking assembly 70 includes an exterior head 72 and at least one, but preferably a pair of cocking elements 74 that extend into the interior chamber 39 through the base 24 of the primary housing 20. The cocking elements 74 are structured to extend into selective, cooperative engagement with the elongate fingers 45' of the retention member so as to urge or pull the lancet receiving assembly 40 into the cocked orientation. To achieve the selective, cooperative engagement, each of the cocking elements 74 preferably includes an inwardly depending abutment 76 that is structured to engage an outwardly extending abutment 48 disposed on the elongate fingers 45' of the retention member. This engagement, however, is structured to be achieved only when the cocking assembly 70 is pulled outwardly away from the primary housing 20. As illustrated in the Figures, the inwardly depending abutments 76 of the cocking assembly 70 are disposed in a generally spaced apart relation from the outwardly extending abutments 48 on the elongate fingers 45' when the lancet receiving assembly 40 is in the cocked orientation, as in FIG. 3. As such, upon release of the lancet receiving assembly 40 from its cocked orientation and its driven movement into the piercing orientation and subsequent fired orientation, the inwardly depending abutments 76 are sufficiently spaced from the outwardly expanding abutments 48 so as to not restrict or in any way hinder the movement of the lancet receiving assembly 40 into that piercing orientation. When, however, the exterior head 72 of the cocking assembly 70 is grasped and pulled, the cocking elements 74 are pulled at least partially out of the interior chamber 39 and the inwardly extending abutments 76 move up and into engagement with the outwardly extending abutments 48 of the retention member 45 such that upon continued movement of the cocking assembly 70 the retention member 45, and accordingly the entire lancet receiving assembly 40, is pulled towards the engagement hub 50 until it is affirmatively coupled with the engagement hub 50. Also in the preferred embodiment of FIG. 3, at least one, but preferably a pair of biased elements 78 are disposed between the base 24 and an outwardly depending element 79 extending from each cocking element 74. These biasing element serve to return and maintain the cocking assembly 70 in its normally retracted orientation when not actually being used for cocking the device, thereby ensuring that the cocking assembly 70 does not hinder or obstruct firing movement of the lancet receiving assembly 40.

Figure 1:
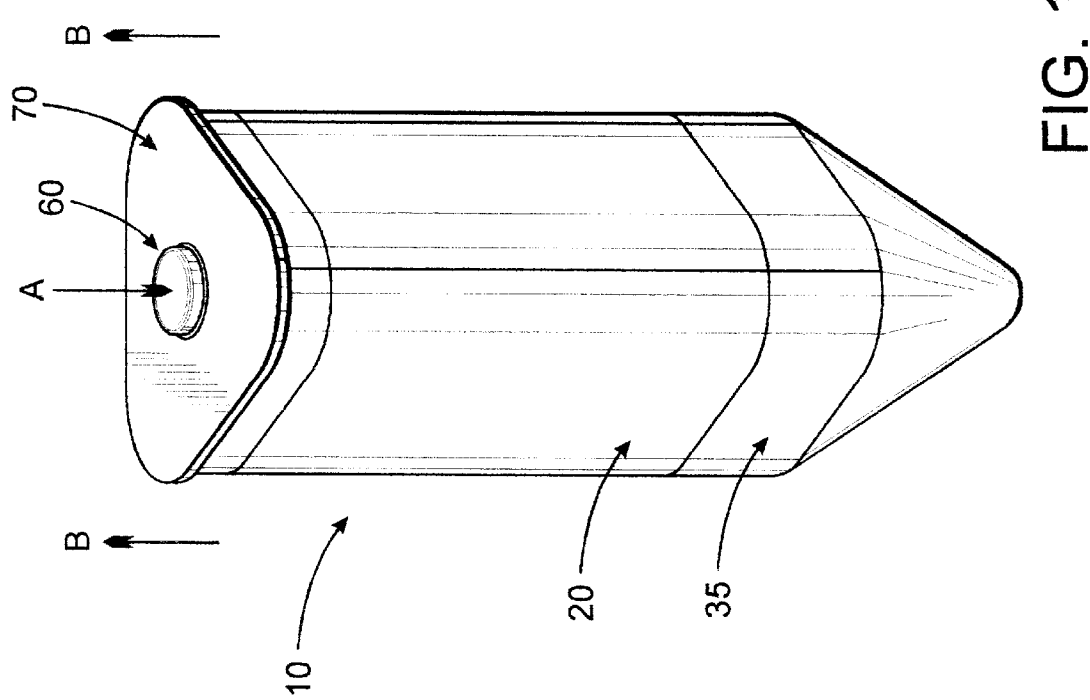
FIG. 1 is a perspective view of the lancet device of the present invention in its cocked orientation.

As an additional advantage of the present invention, as the elongate fingers 45' are urged up into their cooperative engagement with the engagement hub 50, if no pressure is being placed on the actuation assembly 60, the elongate fingers 45' tend to urge the actuation assembly 60 up through the cocking assembly 70 into a ready to actuate orientation, as in FIGS. 1 and 3, wherein the actuation head 62 protrudes above a plane of the exterior head 72 of the cocking assembly 70. In particular, in the preferred embodiment the exterior head 72 of the cocking assembly 70 is disposed in generally surrounding relation to the actuation head 62 of the actuation assembly 60. As such, when the lancet device 10 is in the cocked orientation, the actuation head 62 of the actuation assembly 60 at least partially protrudes beyond a plane of the exterior head 72 of the cocking assembly 70 and provides a substantially clear and easy to identify, tactile identification that the lancet device 10 is in a ready to fire or cocked orientation. When, however, the actuation assembly 60 is actuated or depressed, the actuation assembly 60 tends to retract such that the actuation head 62 drops at least even with, but preferably below a plane of the exterior head 72 of the cocking assembly 70 and is concealed thereby so that the user can easily identify that the lancet device 10 is not ready to fire. Turning to FIG. 4 so as to achieve the effective positioning orientation of the cocking assembly 70 and the actuation assembly 60, it is noted that the base 24 of the primary housing 20 preferably includes a series of apertures 27 and 28 defined therein. In particular, the exterior apertures 27 are structured to receive the cocking elements 74 therethrough, while the interior apertures 28 are structured to receive the wedge elements 64 of the actuation assembly 60 therethrough. Moreover, the base 24 may be integrally molded with the side walls of the primary housing 20, or may comprise a separate element that is secured to the side walls, such as by gluing, a snap fit or any conventional procedure employed on the material(s) utilized to manufacture the primary housing 20.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A lancet device comprising:

a lancet, said lancet including a body portion and a piercing tip extending from said body portion, a primary housing, a cover assembly structured to be matingly coupled with said primary housing so as to define an interior chamber, said cover assembly including a piercing opening, a lancet receiving assembly movably disposed within said interior chamber and structured and disposed to at least temporarily hold said lancet, said lancet receiving assembly being moveable between a cocked orientation and a fired orientation, with movement of said lancet receiving assembly from said cocked orientation to said fired orientation resulting in driven movement of said lancet at least temporarily into a piercing orientation wherein said piercing tip of said lancet protrudes through said piercing opening of said cover assembly, said lancet receiving assembly further including a retention member, an engagement hub disposed in said interior chamber and structured to be cooperatively engaged with said retention member at least upon said lancet receiving assembly being disposed in said cocked orientation so as to maintain said lancet receiving assembly in said cocked orientation until said retention member is affirmatively released from said cooperative engagement therewith, an actuation assembly, said actuation assembly being exteriorly actuatable and being structured and disposed to release said retention member from said cooperative engagement with said engagement hub, said retention member including at least one generally elongate finger, said elongate finger including an inwardly depending protrusion structured to engage cooperative structure on said engagement hub when said lancet receiving assembly is disposed in said cocked orientation, and said actuation assembly being structured to extend at least partially into said interior chamber upon actuation thereof so as to at least temporarily urge said elongate finger out of said engagement with said cooperative structure on said engagement hub.

2. A lancet device as recited in claim 1 wherein said retention member includes two of said elongate fingers disposed in opposite, confronting relation with one another.

3. A lancet device as recited in claim 1 wherein said engagement hub protrudes inwardly from a base of said primary housing and includes a generally enlarged head behind which said inwardly depending protrusion of said elongate finger is cooperatively disposed in order to retain said lancet receiving assembly in said cocked orientation.

4. A lancet device as recited in claim 3 wherein said elongate finger is generally resilient and said actuation assembly includes a wedge element structured to urge said elongate finger at least temporarily into spaced apart relation from said engagement hub, upon actuation of said actuation assembly, such that said inwardly depending protrusion of said elongate finger does not engage said enlarged head of said engagement hub and said lancet receiving assembly is able to freely move out of said cocked orientation.

5. A lancet device as recited in claim 4 further including a biasing element cooperatively disposed with said lancet receiving assembly so as to urge said lancet receiving assembly from said cocked orientation and at least temporarily into said piercing orientation upon release of said elongate finger out of said engagement with said cooperative structure on said engagement hub.

6. A lancet device as recited in claim 5 further including a retraction assembly structured to urge said lancet receiving assembly from said piercing orientation into said fired orientation so as to conceal said piercing tip of said lancet within said interior chamber.

7. A lancet device as recited in claim 6 wherein said retraction assembly includes a resilient material element protruding from said lancet receiving assembly and structured to engage said primary housing such that subsequent to said lancet receiving assembly moving into said piercing orientation, said resilient material element urges said lancet receiving assembly into said fired orientation.

8. A lancet device as recited in claim 5 further including a cocking assembly structured to extend into said primary housing and move said lancet receiving assembly into said cocked orientation.

9. A lancet device as recited in claim 8 wherein said cocking assembly extends through said base of said primary housing and includes at least one cocking element cooperatively engaged with said elongate finger of said retention member so as to urge said lancet receiving assembly which includes said elongate finger into said cocked orientation.

10. A lancet device as recited in claim 9 wherein said cocking element includes an inwardly depending abutment structured to engage an outwardly extending abutment disposed on said elongate finger upon said cocking assembly being at least partially withdrawn from said primary housing, so as to pull said outwardly extending abutment, and accordingly said lancet receiving assembly, towards said base of said primary housing and into said cocked orientation.

11. A lancet device as recited in claim 10 wherein an exterior head of said cocking assembly is normally disposed in generally adjacent relation with said base of said primary housing unless pulled from said housing in order to withdraw said cocking assembly from said primary housing and urge said lancet receiving assembly into said cocked orientation, said inwardly depending abutment of said cocking element being normally disposed in substantially spaced apart relation from said outwardly extending abutment when said cocking assembly is in said normal, generally adjacent relation to said base of said primary housing so as to avoid restricting movement of said lancet receiving assembly from said cocked orientation into said piercing orientation upon release of said retention member from said engaged relation with said engagement hub.

12. A lancet device as recited in claim 11 wherein said exterior head of said cocking assembly is disposed in generally surrounding relation to an exterior actuation head of said actuation assembly, said actuation assembly being structured and disposed to protrude said actuation head from said exterior head of said cocking assembly upon said lancet receiving assembly being disposed in said cocked orientation, and to generally conceal said actuation head at least even with a plane of said exterior head of said cocking assembly when said lancet receiving assembly is disposed in said fired orientation, so as to provide a tactile indication that said lancet receiving assembly is disposed in said cocked orientation.

13. A lancet device as recited in claim 12 wherein said retention member urges said actuation assembly towards said base of said primary housing, such that said actuation head of said actuation assembly protrudes from said exterior head of said cocking assembly, upon said retention member being moved into said cooperative engagement with said engagement hub.

14. A lancet device as recited in claim 1 wherein said primary housing includes a generally triangular configuration so as to facilitate gripping thereof and so as to prevent rolling thereof when disposed on a flat surface.

15. A lancet device as recited in claim 1 further including a retraction assembly structured to urge said lancet receiving assembly from said piercing orientation into said fired orientation so as to conceal said piercing tip of said lancet within said interior chamber.

16. A lancet device as recited in claim 15 wherein said retraction assembly includes a resilient material element protruding from said lancet receiving assembly and structured to engage said primary housing such that subsequent to said lancet receiving assembly moving into said piercing orientation, said resilient material element urges said lancet receiving assembly into said fired orientation.

17. A lancet device as recited in claim 1 further including a cocking assembly structured to extend into said primary housing and move said lancet receiving assembly into said cocked orientation.

18. A lancet device as recited in claim 17 wherein said cocking assembly extends through a base of said primary housing and includes at least one cocking element cooperatively engaged with said elongate finger of said retention member so as to urge said lancet receiving assembly which includes said elongate finger into said cocked orientation.

19. A lancet device as recited in claim 18 wherein said cocking element includes an inwardly depending abutment structured to engage an outwardly extending abutment disposed on said elongate finger upon said cocking assembly being at least partially withdrawn from said primary housing, so as to pull said outwardly extending abutment, and accordingly said lancet receiving assembly, towards said base of said primary housing and into said cocked orientation.

20. A lancet device as recited in claim 19 wherein an exterior head of said cocking assembly is normally disposed in generally adjacent relation with said base of said primary housing unless pulled from said housing in order to withdraw said cocking assembly from said primary housing and urge said lancet receiving assembly into said cocked orientation, said inwardly depending abutment of said cocking element being normally disposed in substantially spaced apart relation from said outwardly extending abutment when said cocking assembly is in said normal, generally adjacent relation to said base of said primary housing so as to avoid restricting the movement of said lancet receiving assembly from said cocked orientation into said piercing orientation upon release of said retention member from said engaged relation with said engagement hub.

21. A lancet device as recited in claim 20 wherein said exterior head of said cocking assembly is disposed in generally surrounding relation to an exterior actuation head of said actuation assembly, said actuation assembly being structured and disposed to protrude said actuation head from said exterior head of said cocking assembly upon said lancet receiving assembly being disposed in said cocked orientation, and to generally conceal said actuation head at least even with a plane of said exterior head of said cocking assembly when said lancet receiving assembly is disposed in said fired orientation, thereby providing a tactile indication that said lancet receiving assembly is disposed in said cocked orientation.

22. A lancet device as recited in claim 21 wherein said retention member urges said actuation assembly towards said base of said primary housing, such that said actuation head of said actuation assembly protrudes from said exterior head of said cocking assembly, upon said retention member being moved into said cooperative engagement with said engagement hub.

23. A lancet device comprising:
  a lancet, said lancet including a body portion and a piercing tip extending from said body portion,
  a primary housing,
  a cover assembly structured to be matingly coupled with said primary housing so as to define an interior chamber,
  said cover including a piercing opening,
  a lancet receiving assembly movably disposed within said interior chamber and structured and disposed to at least temporarily hold said lancet,
  said lancet receiving assembly including a cocked orientation and a fired orientation, movement of said lancet receiving assembly from said cocked orientation to said fired orientation resulting in driven movement of said lancet at least temporarily into a piercing orientation wherein said piercing tip of said lancet protrudes through said piercing opening of said cover assembly,
  said lancet receiving assembly further including a retention member,
  an engagement hub disposed in said interior chamber and structured to be cooperatively engaged with said retention member at least upon said lancet receiving assembly being disposed in said cocked orientation so as to maintain said lancet receiving assembly in said cocked orientation until said retention member is affirmatively released from said cooperative engagement therewith,
  an actuation assembly, said actuation assembly including an exteriorly actuatable actuation head and being structured and disposed to release said retention member from said cooperative engagement with said engagement hub,
  a cocking assembly structured to extend into said primary housing through a base thereof and move said lancet receiving assembly into said cocked orientation,
  said cocking assembly including an exterior head which is normally disposed in generally adjacent relation with said base of said primary housing unless pulled into spaced apart relation from said housing in order to withdraw said cocking assembly from said primary housing and urge said lancet receiving assembly into said cocked orientation, and
  said exterior head of said cocking assembly being disposed in generally surrounding relation to said actuation head of said actuation assembly, said actuation assembly being structured and disposed to protrude said actuation head from said exterior head of said cocking assembly upon said lancet receiving assembly being disposed in said cocked orientation, and to generally conceal said actuation head at least even with a plane of said exterior head of said cocking assembly when said lancet receiving assembly is disposed in said fired orientation, thereby providing a tactile indication that said lancet receiving assembly is disposed in said cocked orientation.

* * * * *